United States Patent
Lambert et al.

(10) Patent No.: US 9,841,394 B2
(45) Date of Patent: Dec. 12, 2017

(54) SYSTEM AND METHOD FOR SENSING OIL QUALITY

(71) Applicant: Pitco Frialator, Inc., Bow, NH (US)

(72) Inventors: Nathaniel A. Lambert, Hookset, NH (US); Owen R. McGhee, Raymond, NH (US); Michael T. Fecteau, Derry, NH (US); Jason D. Finnie, Bow, NH (US); Jared C. Perkins, Chester, NH (US)

(73) Assignee: Pitco Frialator, Inc., Bow, NH (US)

( * ) Notice: Subject to any disclaimer, the term of this patent is extended or adjusted under 35 U.S.C. 154(b) by 22 days.

(21) Appl. No.: 14/942,497

(22) Filed: Nov. 16, 2015

(65) Prior Publication Data

US 2017/0138883 A1    May 18, 2017

(51) Int. Cl.
| | |
|---|---|
| *G01N 27/24* | (2006.01) |
| *G01N 27/06* | (2006.01) |
| *G01N 27/20* | (2006.01) |
| *G01N 33/03* | (2006.01) |

(52) U.S. Cl.
CPC ............ *G01N 27/24* (2013.01); *G01N 27/06* (2013.01); *G01N 27/20* (2013.01); *G01N 33/03* (2013.01)

(58) Field of Classification Search
CPC ... G01N 27/22; G01N 27/221; G01R 27/2605
USPC ........................................................ 324/663
See application file for complete search history.

(56) References Cited

U.S. PATENT DOCUMENTS

| | | | |
|---|---|---|---|
| 4,148,729 A | 4/1979 | Howard | |
| 4,210,123 A | 7/1980 | Moore et al. | |
| 4,324,173 A | 4/1982 | Moore et al. | |
| 4,506,995 A | 3/1985 | Polster | |
| 4,688,475 A | 8/1987 | Witt et al. | |
| 4,742,455 A | 5/1988 | Schreyer | |
| 4,764,258 A | 8/1988 | Kauffman | |
| 4,908,676 A | 3/1990 | Bedell et al. | |
| 4,959,144 A * | 9/1990 | Bernard ............... | A47J 37/1223 210/232 |
| 5,071,527 A | 12/1991 | Kauffman | |
| 5,160,444 A | 11/1992 | McFarland | |
| 5,179,891 A | 1/1993 | Chiu | |
| 5,239,258 A | 8/1993 | Kauffman | |

(Continued)

FOREIGN PATENT DOCUMENTS

| | | |
|---|---|---|
| DE | 27 46 728 | 4/1979 |
| DE | 82 3 081.5 | 4/1990 |

(Continued)

OTHER PUBLICATIONS

International Search Report for PCT/US2016/061982, dated Jan. 31, 2017, 2 pp.

(Continued)

*Primary Examiner* — Jermele M Hollington
*Assistant Examiner* — Christopher McAndrew
(74) *Attorney, Agent, or Firm* — Brinks Gilson & Lione

(57) ABSTRACT

A system for measuring the state of degradation of cooking oil in a deep fryer is provided. The system includes a filter system with a filter vat, a filter media, and a filter pump. A sensor is disposed with respect to the vat or the piping associated with the filter system, the sensor being adapted to measure an electrical property that is indicative of total polar materials of said cooking oil.

22 Claims, 3 Drawing Sheets

(56) References Cited

U.S. PATENT DOCUMENTS

| | | | |
|---|---|---|---|
| 5,247,876 | A | 9/1993 | Wilson et al. |
| 5,404,799 | A | 4/1995 | Bivens |
| 5,523,692 | A | 6/1996 | Kuroyanagi et al. |
| 5,594,327 | A | 1/1997 | Sagredos et al. |
| 5,617,777 | A | 4/1997 | Davis et al. |
| 5,776,530 | A | 7/1998 | Davis et al. |
| 5,787,372 | A | 7/1998 | Edwards et al. |
| 5,818,731 | A * | 10/1998 | Mittal ............ A47J 37/1266 702/22 |
| 5,929,754 | A | 7/1999 | Park et al. |
| 5,933,016 | A | 8/1999 | Kauffman et al. |
| 5,942,269 | A | 8/1999 | Casey et al. |
| 5,951,854 | A | 9/1999 | Goldberg et al. |
| 5,954,933 | A | 9/1999 | Ingalls et al. |
| 6,009,974 | A | 1/2000 | Casey et al. |
| 6,127,185 | A | 10/2000 | Melton et al. |
| 6,235,210 | B1 | 5/2001 | Saksena |
| 6,274,850 | B1 | 8/2001 | Mercer |
| 6,278,282 | B1 | 8/2001 | Marszalek |
| 6,378,420 | B1 | 4/2002 | Savage et al. |
| 6,436,713 | B1 | 8/2002 | Onwumere et al. |
| 6,455,085 | B1 | 9/2002 | Duta |
| 6,459,995 | B1 | 10/2002 | Collister |
| 6,469,521 | B1 | 10/2002 | Klun et al. |
| 6,553,812 | B2 | 4/2003 | Park et al. |
| 6,600,306 | B1 | 7/2003 | Pernot et al. |
| 6,602,533 | B1 | 8/2003 | Smith et al. |
| 6,717,667 | B2 | 4/2004 | Abraham et al. |
| 6,745,669 | B2 | 6/2004 | Suzuki |
| 6,777,009 | B1 | 8/2004 | Shealy |
| 6,783,685 | B2 | 8/2004 | Hwang |
| 6,791,334 | B2 | 9/2004 | Horie et al. |
| 6,822,461 | B2 | 11/2004 | Klun |
| 6,873,916 | B2 | 3/2005 | Kolosov et al. |
| 6,958,166 | B2 | 10/2005 | Taylor |
| 7,019,654 | B2 | 3/2006 | Danyluk et al. |
| 7,030,629 | B1 | 4/2006 | Stahlmann et al. |
| 7,043,967 | B2 | 5/2006 | Kauffman et al. |
| 7,043,969 | B2 | 5/2006 | Matsiev et al. |
| 7,129,715 | B2 | 10/2006 | Hayashi et al. |
| 7,132,079 | B2 | 11/2006 | Onwumere et al. |
| 7,158,897 | B2 | 1/2007 | Kolosov et al. |
| 7,210,332 | B2 | 5/2007 | Kolosov et al. |
| 7,225,081 | B2 | 5/2007 | Kolosov et al. |
| 7,239,155 | B2 | 7/2007 | Byington et al. |
| 7,254,990 | B2 | 8/2007 | Matsiev et al. |
| 7,287,431 | B2 | 10/2007 | Liu et al. |
| 7,383,731 | B2 | 6/2008 | Liu et al. |
| 7,390,666 | B2 | 6/2008 | Onwumere et al. |
| 7,407,566 | B2 | 8/2008 | Jiang et al. |
| 7,504,835 | B2 | 3/2009 | Byington et al. |
| 7,504,836 | B2 | 3/2009 | Chambon et al. |
| 7,521,945 | B2 | 4/2009 | Hedges et al. |
| 7,523,006 | B2 | 4/2009 | Muhl et al. |
| 7,523,646 | B2 | 4/2009 | Klun |
| 7,600,424 | B2 | 10/2009 | Sasaki et al. |
| 7,652,490 | B2 | 1/2010 | Muhl et al. |
| 7,719,289 | B2 | 5/2010 | Muhl et al. |
| 7,729,870 | B2 | 6/2010 | Sun |
| 7,834,646 | B2 | 11/2010 | Chambon et al. |
| 7,928,741 | B2 | 4/2011 | Hedges et al. |
| 8,207,749 | B2 | 6/2012 | Reime |
| 8,257,976 | B2 | 9/2012 | Wei et al. |
| 8,287,182 | B2 | 10/2012 | Muhl et al. |
| 8,325,345 | B2 | 12/2012 | Mahmoodi et al. |
| 8,340,928 | B2 | 12/2012 | Sun |
| 8,421,486 | B2 | 4/2013 | Akiyama et al. |
| 8,432,171 | B2 | 4/2013 | Coppe et al. |
| 8,436,629 | B2 | 5/2013 | Chambon |
| 8,497,691 | B2 * | 7/2013 | Behle ............ A47J 37/1223 324/663 |
| 8,505,443 | B2 | 8/2013 | Abney et al. |
| 8,519,726 | B2 | 8/2013 | Sun |
| 8,551,331 | B2 | 10/2013 | Burkett et al. |
| 8,564,310 | B2 | 10/2013 | Yu et al. |
| 8,614,588 | B2 | 12/2013 | Hedges |
| 8,643,388 | B2 | 2/2014 | Hedges |
| 8,689,679 | B2 | 4/2014 | Tiszai et al. |
| 8,709,260 | B2 | 4/2014 | Burkett et al. |
| 8,732,938 | B2 | 5/2014 | Kolosov et al. |
| 8,736,282 | B2 | 5/2014 | Chambon |
| 8,764,967 | B2 | 7/2014 | Fan |
| 8,773,152 | B2 | 7/2014 | Niemann et al. |
| 8,828,223 | B2 | 9/2014 | Savage et al. |
| 8,829,928 | B2 | 9/2014 | Gonzalez et al. |
| 8,847,120 | B2 | 9/2014 | Burkett et al. |
| 8,854,058 | B2 | 10/2014 | Katafuchi |
| 8,980,102 | B2 | 3/2015 | Florkey et al. |
| 9,038,443 | B1 | 5/2015 | Pace et al. |
| 9,161,659 | B2 | 10/2015 | Lambert et al. |
| 9,170,144 | B2 | 10/2015 | Qi |
| 9,176,086 | B2 | 11/2015 | Qi |
| 9,228,965 | B2 * | 1/2016 | Burkett ............ A47J 37/1266 |
| 9,510,708 | B2 | 12/2016 | Behle et al. |
| 2002/0035931 | A1 | 3/2002 | Tschopp et al. |
| 2002/0046657 | A1 * | 4/2002 | Takahashi ............ A47J 37/1223 99/330 |
| 2002/0069767 | A1 | 6/2002 | Wendel et al. |
| 2002/0082924 | A1 | 6/2002 | Koether |
| 2004/0250622 | A1 | 12/2004 | Kolosov et al. |
| 2005/0153022 | A1 | 7/2005 | Schilling et al. |
| 2005/0247697 | A1 | 11/2005 | Wu |
| 2006/0254432 | A1 | 11/2006 | McLemore |
| 2007/0272209 | A1 | 11/2007 | Matsiev et al. |
| 2008/0121578 | A1 | 5/2008 | Burkett et al. |
| 2008/0196596 | A1 | 8/2008 | Forrest et al. |
| 2008/0213446 | A1 | 9/2008 | Feinberg et al. |
| 2008/0238445 | A1 | 10/2008 | Muhl et al. |
| 2008/0282905 | A1 | 11/2008 | Savage et al. |
| 2009/0044721 | A1 | 2/2009 | Claesson et al. |
| 2009/0252842 | A1 | 10/2009 | Wang et al. |
| 2009/0309619 | A1 * | 12/2009 | Behle ............ A47J 37/1223 324/698 |
| 2010/0000418 | A1 | 1/2010 | Payen et al. |
| 2010/0201528 | A1 | 8/2010 | Bruinsma et al. |
| 2010/0260903 | A1 | 10/2010 | Wei et al. |
| 2011/0030486 | A1 | 2/2011 | Hall et al. |
| 2011/0084708 | A1 | 4/2011 | Yu |
| 2011/0234244 | A1 | 9/2011 | Chambon |
| 2011/0238310 | A1 | 9/2011 | Estrellado et al. |
| 2011/0267080 | A1 | 11/2011 | Hedges |
| 2012/0022694 | A1 | 1/2012 | Mohanty et al. |
| 2012/0062251 | A1 | 3/2012 | Gonzalez et al. |
| 2012/0074125 | A1 | 3/2012 | Burkett et al. |
| 2012/0075115 | A1 | 3/2012 | Lee et al. |
| 2012/0229151 | A1 | 9/2012 | Katafuchi |
| 2012/0229152 | A1 | 9/2012 | Katafuchi |
| 2013/0036916 | A1 * | 2/2013 | Burkett ............ A47J 37/1266 99/330 |
| 2013/0214797 | A1 | 8/2013 | Gruden |
| 2013/0278276 | A1 * | 10/2013 | Behle ............ A47J 37/1223 324/663 |
| 2014/0130579 | A1 | 5/2014 | Hedges |
| 2014/0130900 | A1 | 5/2014 | Hedges |
| 2014/0188404 | A1 | 7/2014 | Von Herzen et al. |
| 2014/0188407 | A1 | 7/2014 | Von Herzen et al. |
| 2014/0266065 | A1 | 9/2014 | Von Herzen et al. |
| 2015/0027205 | A1 | 1/2015 | Brugger |
| 2015/0272390 | A1 | 10/2015 | Burns et al. |
| 2015/0285777 | A1 | 10/2015 | Baumann et al. |

FOREIGN PATENT DOCUMENTS

| | | |
|---|---|---|
| DE | 298 12 263 U1 | 10/1998 |
| DE | 199 47 669 A1 | 5/2001 |
| DE | 100 53 250 A1 | 11/2002 |
| DE | 20 2005 007144 U1 | 7/2005 |
| DE | 10 2005 039480 A1 | 3/2007 |
| DE | 10 2006 003733 B3 | 3/2007 |
| EP | 0 561 583 A1 | 3/1993 |
| EP | 1 004 872 A1 | 5/2000 |
| JP | 2003 250708 A | 9/2003 |
| JP | 2005-055198 A | 3/2005 |

(56) References Cited

FOREIGN PATENT DOCUMENTS

| WO | WO 02/04914 A2 | 1/2002 |
|---|---|---|
| WO | WO 2007/055980 A1 | 5/2007 |
| WO | WO 2010/076839 A2 | 8/2010 |
| WO | WO 2012/012747 A2 | 1/2012 |
| WO | WO 2012/027304 A1 | 3/2012 |
| WO | WO 2012/031924 A1 | 3/2012 |
| WO | WO 2012/036964 A2 | 3/2012 |
| WO | WO 2013/036813 A1 | 3/2013 |
| WO | WO 2013/139354 A1 | 9/2013 |
| WO | WO 2014/167158 A1 | 10/2014 |
| WO | WO 2014/167159 A1 | 10/2014 |
| WO | WO 2014/181209 A1 | 11/2014 |
| WO | WO 2015/090359 A1 | 6/2015 |
| WO | WO 2015/142283 A1 | 9/2015 |
| WO | WO 2015/147886 A1 | 10/2015 |

OTHER PUBLICATIONS

Written Opinion for PCT/US2016/061982, dated Jan. 17, 2017, 8 pp.

Written Opinion of the International Searching Authority for PCT/US2015/037927, dated Oct. 8, 2015, 7 pp.

International Search Report for PCT/US2015/037927, dated Oct. 12, 2015, 4 pp.

Deep Frying-Chemistry, Nutrition, and Practical Applications, $2^{nd}$ Edition, Michael D. Erickson, Editor, "Evaluation of Used Frying Oil" by Frank T. Orthoefer and Gary R. List, pp. 329-342, 19 pp.

Journal of Food Process Engineering, D.R. Heldman and R.P.Singh, CoEditors, Food & Nutrition Press, Inc., vol. 19, No. 2, Jun. 1996, "Dynamics of Fat/Oil Degradation During Frying Based on Physical Properties" by S. Paul and G. Mittal, pp. 201-221, 24 pp.

European Journal of Lipid Science and Technology, Official Journal of the European Federation for the Science and Technology of Lipids (Euro Fed Lipid), Special Topic: Deep Fat Frying—Healthier and Tastier Fried Food, Nov. 2004, "Tests to monitor quality of deep-frying fats and oils" by Richard F. Stier, pp. 766-771, www.ejlst.de, 9 pp.

English Translation of JP 2005-055198 for "Fat and Oil Degradation Detector and Fryer" submitted in IPR 2016-01435, 11 pp.

International Search Report and Written Opinion for PCT/US2016/067179, dated May 12, 2017, 11 pp.

International Preliminary Report on Patentability for International Application No. PCT/US2015/037927, dated Jan. 3, 2017, 8 pp.

* cited by examiner

SYSTEM AND METHOD FOR SENSING OIL QUALITY

TECHNICAL FIELD

This disclosure relates to systems for measuring the quality of oil associated with a cooking appliance, such as a deep fat fryer.

BRIEF SUMMARY

A representative embodiment of the disclosure is provided. The representative embodiment includes a system for measuring the state of degradation of cooking oil. The system includes a vat with a receiving space configured for receipt of cooking oil, the vat comprising a filtering media, the vat remote from a device used to cook food product with cooking oil. A pump is in fluid communication with the vat, the pump taking suction from the receiving space. A sensor is disposed in fluid communication within the vat and adapted to measure an electrical property that is indicative of the quality of the cooking oil within the vat.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
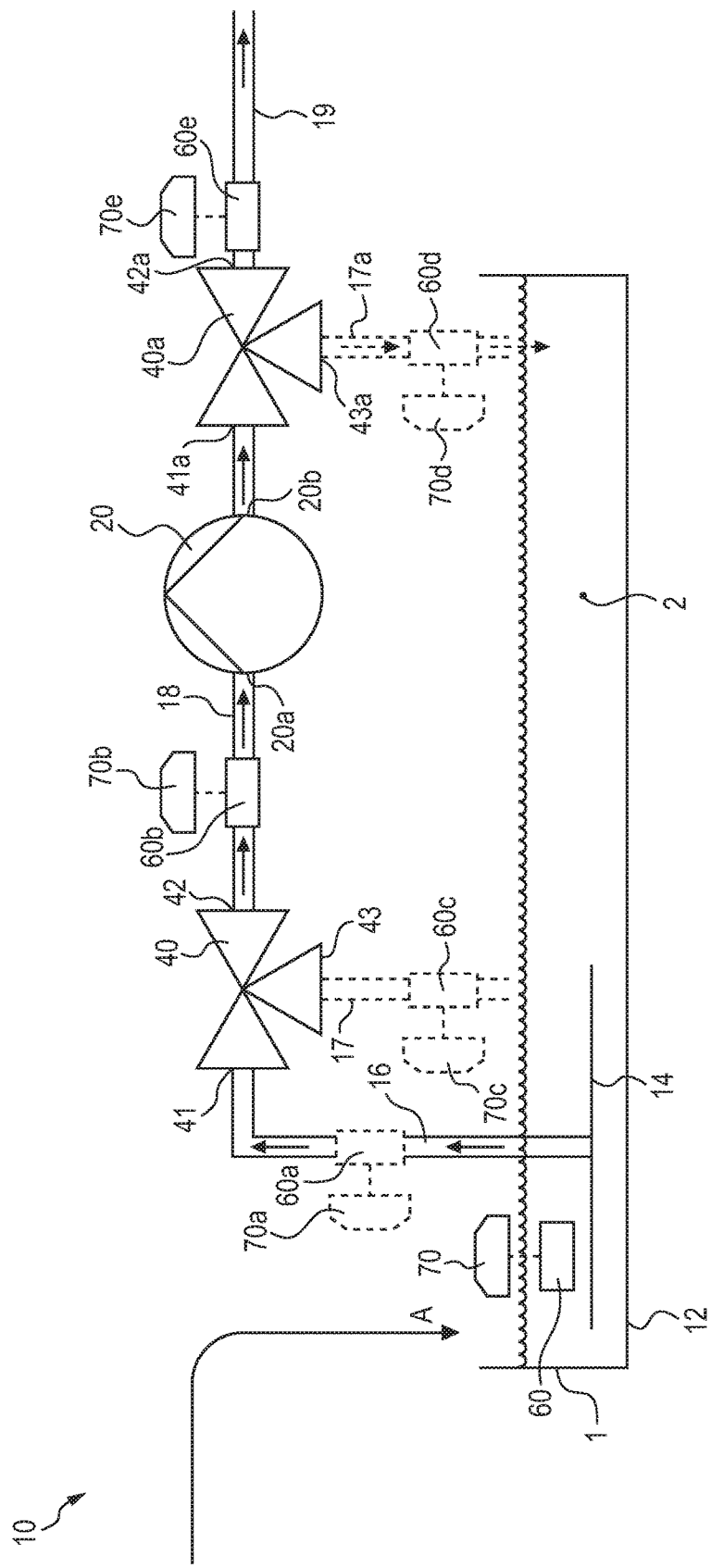
FIG. 1 is a schematic view of an oil filtering system depicting an oil sensing system in several potential positions within the oil filtering system.
Figure 2:
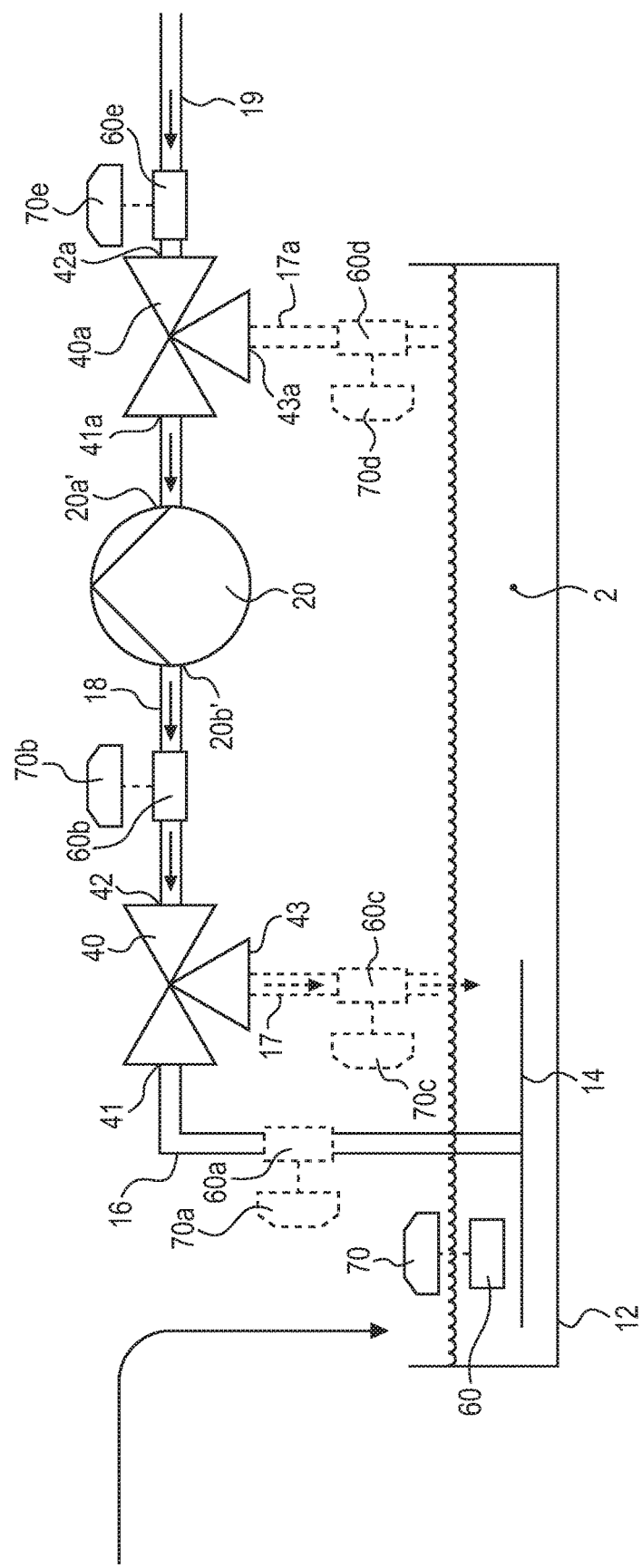
FIG. 2 is a schematic view of the oil filtering system of FIG. 1 aligned for operation in a different manner.
Figure 3:
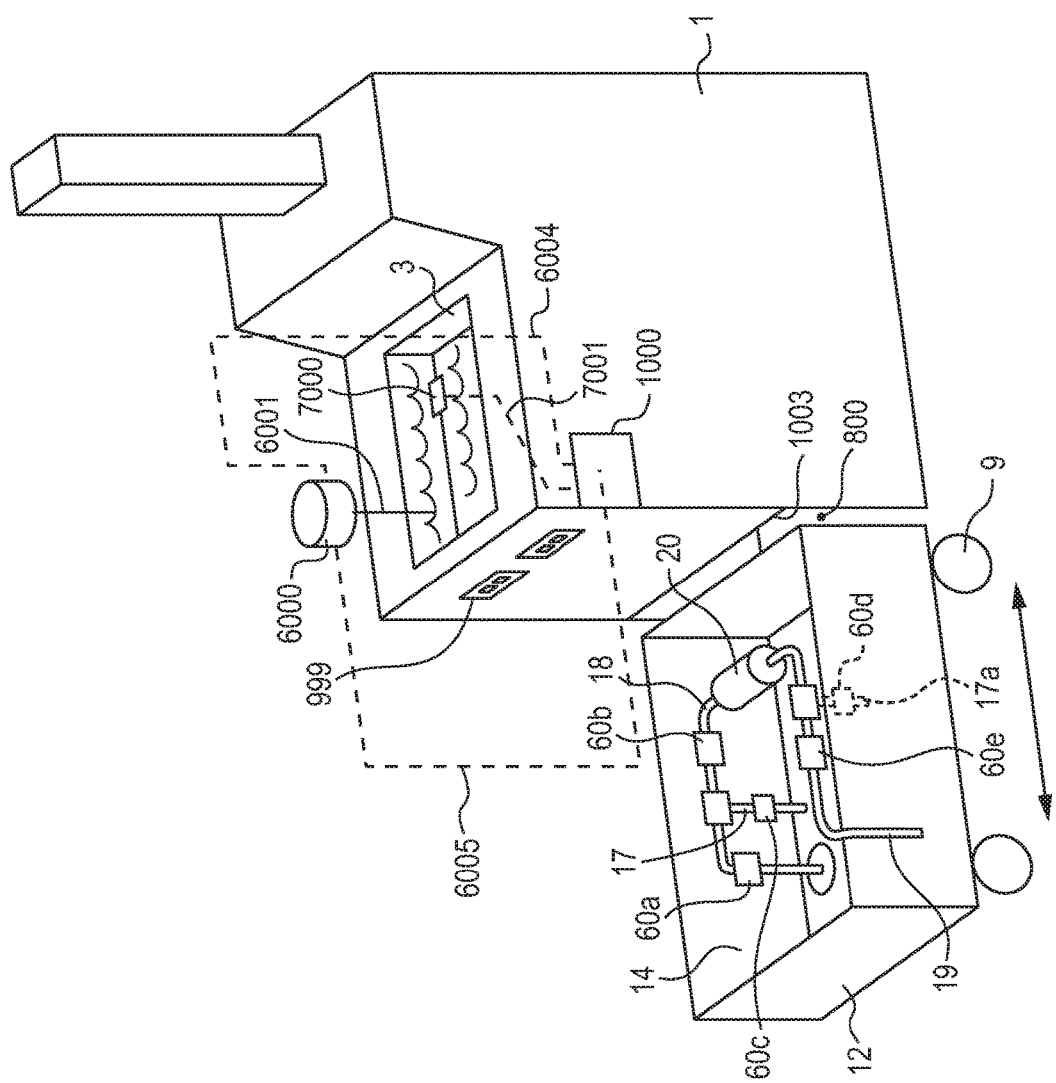
FIG. 3 is a schematic view of a fryer with the oil sensing system of FIG. 1.

Turning now to FIGS. 1-3, a system 10 for sensing the quality of oil that is associated with a cooking appliance 1 is provided. The system 10 may be fluidly connected to a cooking appliance, such as deep fat fryer 1, such that the system 10 can be either be continuously, cyclically, or manually used to measure the quality of oil that is representative of the oil located in the cooking device.

In some embodiments, the system 10 may be associated with a filtering system for a cooking appliance, such as a portable filter pan, as shown schematically in the figures. The portable filter pan 2 may include a vat 12 for receiving and holding cooking oil with a receiving space and that supports a filter 14 material 14. The filter material 14 is configured to remove foreign matter, crumbs and/or other impurities from the oil disposed within the vat that passes through the filter material. The filter material 14 may be a conventional filter for cooking oil, such as with one or more of a filter screen, a mesh, a paper, or a fabric that is used to mechanically and/or chemically remove particles and impurities from oil (due to oxidation or hydrolysis, for example) within the vat 12, and specifically as oil passes through the filtering material.

The vat 12 of the portable filter may receive oil that is drained from the cooking appliance 1, and specifically from the container that holds the oil within the cooking device, such as a frypot for a conventional deep fat fryer. The vat 12 may be configured to receive cooking oil from a plurality of different cooking appliances that are used in the same facility, such as a bay of frypots used within a bank of deep fat fryers.

The vat may be rigidly fixed to a cooking appliance 1, such as within the housing in a space 800 below a frypot 3 and equipment used to heat the oil within the frypot 3, such as a gas burner system (not shown). In some embodiments, the vat 12 may be slidably or rollably mounted upon the housing of the cooking appliance such that the vat is normally disposed within or directly below the housing, such as during cooking operations of the cooking appliance, and may be slid out of at least a portion of the housing to allow for easy access to the components of device 10. FIG. 3 is provided to show the vat 12 slid (or rolled) out of the housing of the cooking appliance 1, and one of ordinary skill in the art will understand that the vat 12 can be moved (in the direction X) to within the housing. In some embodiments, the vat 12 rests upon a plurality of wheels or castors 9, while in other embodiments, the vat 12 is movably supported upon rails that are associated with the housing. The device 1 may be configured such that the vat 12 can receive oil to be filtered from the cooking appliance when the vat 12 is either disposed within the housing of the cooking appliance or when the vat is moved partially or fully outside of the housing for the cooking appliance.

The vat 12 may support a pump 20 that is fluidly connected to the vat 12, and specifically to a volume of oil that is disposed within the vat 12. In some embodiments, a suction 20a of the pump (FIG. 1) is fluidly connected with the vat such as to take suction from the vat, and a discharge 20b of the pump 20 extends away from the vat 12, such as to direct oil to exit the system 10 and, if aligned with respect to a cooking device, to return the cooking oil to the cooking device, such as the frypot of a deep fat fryer. As shown schematically in FIG. 3, the discharge 20b of the pump may be fluidly connected to a return hose or pipe 19. In some embodiments, device may be configured such that the discharge 20b of the pump 20 is aligned to direct oil to a disposal container, or to another frypot, different from the frypot from which the oil in the vat 12 was received. In some embodiments shown in FIG. 2, the pump 20 may be operable in the opposite direction, such that the pump 20 discharge 20b' is fluidly connected (assuming that the valve 40 is aligned for flow from the second port 42 to the first port 43, such that oil is pumped to the vat 12. One of ordinary skill in the art, with a thorough review of this specification and drawings, will understand that the device 10 can be aligned (with differing pumping directions and valve positions, discussed herein) for flow in various directions and sensing oil quality with various sensors 60, 60a, etc. for different operational needs in conjunction with filtering.

In some embodiments, a valve 40 (40a) may be provided that is disposed with respect to the pump 20 and the vat 12. In some embodiments, the valve 40 may be positioned upstream of the pump 20, such that the valve 40 is fluidly connected to the suction 20a of the pump 20, while in other embodiments, the valve may be positioned (as shown as 40a in FIG. 1) such that it is fluidly connected to the discharge 20b of the pump 20. In some embodiments, the valve 40a may be provided instead of valve 40, while in other embodiments, both valve 40 and valve 40*a* may be provided on opposite sides of the pump 20. In some embodiments, the valve 40 (40*a*) may be a valve with a single inlet and a single outlet.

In some embodiments, the valve 40 may be a three way valve that can be selectively aligned for the desired flow through the system 10. For example, the valve 40 may have a first port 41 that is fluidly connected to a pick up tube 16, which is fluidly connected to the vat 12, and specifically the pick up tube 16 may be fluidly connected to the filter 14 such that oil that flows through the pick up tube 16 has passed through the filter 14. The valve 40 may have a second port 42 that is fluidly connected to the suction 20*a* of the pump 20. The valve 40 may have a third port 43 that is fluidly connected to a return 17 that directs oil to the vat 12. In some embodiments, the valve 40 (40*a*) is aligned such that flow from the first port 40*a* is directed to one of the second and third ports 40*b*, 40*c*, but not to both ports simultaneously. In other embodiments, the valve 40 (40*a*) may be aligned such that a portion of the cooking oil that flows into the valve through the first port flows through each of the second and third ports 40*b*, 40*c*.

In embodiments when the valve 40*a* is provided, the valve 40*a* may be a three way valve and be constructed in a similar manner as the valve 40 discussed above, although the various ports of the valve 40*a* are connected to different components of the system 10. For example, the valve 40*a* may have a first port 41*a* that is fluidly connected to the discharge 20*b* of the pump 20, a second port 42*a* that is fluidly connected to return piping 19 (discussed elsewhere herein), and a third port 43*a* that is fluidly connected to a return 17*a* that directs oil to the vat 12.

One or both of the valves 40, 40*a* may be manually operated to allow the valve to be aligned for flow in the desired direction, such as from the first port 41 to the second port 42, or from the first port 41 to the third port 43. In some embodiments, one or both of the three way valves 40, 40*a* may be automatically operable, such as via an automatic operator associated with the valve to allow for the operator to control the position of the valve (either remotely or at the valve) but without the user needing to physically reposition the valve. In some embodiments a controller 1000 (shown schematically in FIG. 3 may be provided that sends a signal to the valve 40 (40*a*) to be repositioned, either based upon instructions from the user or automatically generated by the controller 1000. While the controller 1000 is depicted in FIG. 3 schematically as being a part of the cooking appliance 1, the controller 1000 could be a part of the device 10.

One or more sensors 60 may be provided at one or more locations within the device that receives oil during operation of the system. The sensor 60 may be provided at a location that is in fluid communication with the vat 12, such that the sensor measures a parameter (discussed below) of the oil within the vat 12 (or after passing through the filter 14. Because the device 1 is configured to filter oil that is received from a cooking device, such as a deep fat fryer, and upon filtering the oil return the newly filtered oil to the cooking device, the parameter of the oil measured by the sensor 60 is representative of the quality of the oil that eventually would be returned to the cooking device for use with cooking a food product.

As discussed above, the sensor 60 may be provided in many different positions within the device. FIG. 1 depicts the sensor 60 in multiple different positions within the device. One of the possible locations for the sensor is identified with the element number 60, while other potential locations for the sensor are depicted with the element number 60 and a corresponding letter, such as 60*a*, 60*b*, etc. The specific locations of for sensors that are depicted in the figures are disclosed herein. It is contemplated that the device may include only one sensor, which may be at any desired location of the possible locations discussed herein and depicted in the figures, or in some embodiments, more than one sensor (at two or more of the locations) may be provided within the device. Unless described herein to the contrary, each sensor depicted in the figures and described herein shall be the same in structure and operation as the sensor 60 described below.

The sensor 60 may be an electrical sensor that is adapted to continuously measure one or more electrical parameters of oil which are directly indicative, or representative of the amount of impurities in the oil flowing through/past the sensor 60. For example, it is a well-known attribute of cooking oil to measure the total polar materials, or total polar compounds, therewithin and it is known that the amount of total polar materials/compounds increases as the life of the cooking oil decreases (i.e. the amount of total polar materials/compounds increases as the oil is used for longer time periods). The sensor 60 may be configured to continuously measure the capacitance of the oil flowing past/through the sensor, which is representative of the total polar materials/compounds in the oil, due to the known proportionality between the total polar materials/compounds in the oil and the dielectric constant of the oil. Still further, the sensor may be configured to measure voltage, resistance, dielectric, conductivity, or conductance of the oil, some or all of which may be indicative of total polar materials or other aspects of oil that relate to the overall quality of the oil, and in some embodiments, the sensor may be configured to measure more than one (or all) of these parameters.

The oil sensor may be a coaxial sensor, or a resonant sensor, or another type of sensor known in the art to be capable of sensing one or more electrical parameters of oil (such as those listed above) in order for the sensor to determine the total polar compounds/materials within the oil to allow for an oil quality determination to be made, such as by a controller 1000.

As depicted in FIG. 1, the sensor 60 may include an antenna 70 that is configured to send a signal that is proportional to the parameter(s) of the oil measured by the sensor 60 to the display 999 or to the controller 1000. The antenna 70 may be configured to pass a wireless signal (such as through WiFi, Bluetooth, or other wireless transmission systems) and/or may pass a signal via a wired interface. As with the sensors, the antenna 70 may be provided with the sensor regardless of the position of the sensor 60 within the device, and for the sake of clarity, each sensor in different possible positions (e.g. 60*a*, 60*b*, etc.) is drawn with a corresponding antenna with the same reference character (e.g. 70*a*, 70*b*, etc.). As with the sensors 60, 60*a*, etc., the antennas, regardless of position, may operate in the same manner as the antenna 70 discussed above.

With reference to FIG. 1 and as mentioned above, the sensor 60 (and antenna 70 when provided) can be provided in numerous different positions with respect to the device 10. For example, the sensor 60 may be provided to interact with oil that rests within the vat 12. Alternatively or additionally, the sensor 60*a* may be provided to interact with oil that flows through the take up pipe 16 that receives oil that has passed through the filter 14 and prior to the oil reaching the first valve 40 (when provided), or prior to reaching the suction 20a of the pump. Still alternatively or additionally, the senor 60b may be provided between the first valve 40 and the suction 20a of the pump.

Still alternatively or additionally, the sensor 60c may be provided in fluid communication with the third port 43 of the first valve 40 such that the oil that interacts with the sensor 60c is directed to return to the vat 12. Alternatively or additionally, the sensor 60d may be provided in fluid communication with the third port 43a of the second valve 40a, such that oil that interacts with the sensor 60d is directed to return to the vat 12. Finally, alternatively or additionally, the sensor 60e may be provided proximate to the second port 42a of the second valve (when provided, or alternatively downstream of the discharge 20b of the pump 20), such that the sensor 60e interacts with oil that is urged by the pump 20, such as to return to the cooking appliance 1, or to another vessel such a different cooking appliance or a vessel (not shown) for storage.

The sensor 60 may be configured to measure the parameter of the oil as oil flows past the sensor as urged by the pump 20 or as urged by gravity, and/or when oil is still with respect to the sensor. In the latter case (oil parameter is measured when the oil is still), the sensor 60b may be provided and the first valve 40 may be aligned such that the valve is ported for fluid communication between the first and third ports 41, 43, with the second port being closed. This alignment of the second valve in combination with the pump 20 being secured causes a slug of oil within the pipe 18 to remain still. In some embodiments, the second valve 40a, when provided, may also be aligned to prevent flow through the first port 41a.

In some embodiments, the sensor 60 may provide a signal to the display 999 that is indicative of the measured electrical property of the oil, such that the display 999 can provide a measured value of the oil to the user to allow the user to take action, such as by adjusting the position of a valve 40 (40a), such as to continue filtering the oil through the filter material 14, such as by aligning the second valve 40a to flow from the first port 41a to the third port 43a to return to the vat 12 to pass through the filter an additional time.

In some embodiments, the sensor 60 (or multiple sensors) may provide a signal to the display 999 (in some embodiments by way of the antenna) that is representative of the rate of change of the value of the measured parameter, such that the user when viewing the display can understand whether the filter material 14 is working correctly to improve the quality of the oil (such as by removing impurities or crumbs) with continued filtration, or whether the filter material needs to be cleaned or whether the filter material may have reached the end of its useful life.

In some embodiments, the sensor 60 may additionally or alternatively provide a signal to the controller 1000 that is representative of the measured parameter(s) of the oil, and/or representative of the rate of change of the measured parameter(s). In these embodiments, the controller 1000 may compare the signal from the sensor (which may be by way of the antenna 70) with a reference value (or range) of the measured parameter(s). If the controller 1000 detects that the measured property is satisfactory (such as it is above or below a setpoint, or it is within a programmed acceptable range), the controller may provide an indication to the user that the oil quality is acceptable, such as on the display 999 associated with the cooking device 1, upon the device 1, or on a remote device. In some embodiments, when the controller determines that the measured parameter is within an acceptable range, the controller may cause the first and/or second valves 40, 40a to be positioned such that flow extends from the first port 41 to the second port 42 and closes the third port 43, while when the controller determined that the measured parameter is outside of an acceptable range, the controller may cause the first and/or second valves 40, 40a to be positioned such that flow extends from the first port 41 to the third port 43, such that oil is returned to the vat 12 for additional filtering, and/or disposal.

Turning now to FIG. 3, a system for calibration of the sensor 60 is provided. The system may include all of the components of the device 10 discussed above, such as a filter pan 80, the pump 20, the valves 40, 40a, and one or more of the sensors 60. The system may further include a controller 1000, which, as discussed above, may receive a signal 1003 from the sensor 60 that is indicative of the measured electrical property of the oil. In some embodiments the signal 1003 may be a raw digital or analog signal (such as a voltage that changes based upon the magnitude of the measured parameter) that is representative of the measurement taken by the sensor 60, with the controller 1000 receiving the raw signal and converting it to a measured property. In other embodiments, the signal 1003 may be a signal that is the value of the actual parameter being measured. In other words, in some embodiments, the sensor 60 may supply a signal 1003 that must be processed and analyzed by the controller to determine the value of the parameter being measured (conductivity, dielectric constant, etc.), and in some embodiments evaluated by the controller 1000 to determine whether a signal, indication, or alarm should be provided to the user (through signal 1001).

In either of the above possibilities initial and/or periodic or routine calibration of the sensor 60 must be performed to ensure that the measured electrical property (by the sensor 60) is indicative of the same electrical property of the actual oil. It is known in the art that the electrical characteristics of sensors (and processing equipment) may vary over time based upon factors such as changing internal resistance, fouling of the surface of a sensor's electrodes, or for other reasons. Due to these or any other changes in the sensor's operation (or possibility changes in the wiring or path for an analog signal transmission to the controller), it is important to periodically assess the proper operation of the sensor and recalibrate the sensor as necessary.

For example, in some embodiments, a portable sensor 6000 (shown schematically in FIG. 3) that measures the same electrical property of the oil as measured by the sensor 60 may be provided, such as measuring with in the vat 12 or in the frypot. The sensor 6000 may include a probe 6001 may be used to measure the electrical characteristic of the oil. The portable sensor 6000 may provide a direct reading of the measured electrical characteristic upon its display. Alternatively or additionally, the portable sensor 6000 may provide a signal 6004 to the controller 1000 that is representative of the measured electrical characteristic (either the signal 6004 being the actual value of the measured electrical characteristic, or a measurement that is representative of the measured characteristic, similar to the sensor 60 as discussed above). In embodiments where the portable sensor 6000 is used, assuming that the calibration of the portable sensor 6000 was recently verified, the controller 1000 receives the value of the measured parameter via the signal 6004 and compares the measured parameter from the portable sensor 6000 with the value of the measured parameter from the sensor 60 as received by the controller 1000. If there is any difference between the values of the measured parameter from the portable sensor 6000 and the sensor 60, the controller 1000 can automatically adjust the gain (or another adjustable parameter) of the sensor 60 to calibrate the output of the sensor 60 (by sending a signal to the antenna to cause the gain adjustment within the sensor 60), or alternatively or additionally modify the controller's processing of the signal 1003 received from the sensor 60 such that the value of the measured parameter of the sensor 60 is consistent with the measured value of the sensor 6000, in order for the measurement taken by the sensor 60 to reflect the "accurate" measurement of the same parameter using the portable sensor 6000.

Various calibration techniques that could be implemented by the controller 1000 to adjust the calibration of the sensor 60 (such adjusting the gain, or the input voltage of the sensor 60) are well known in the art and will not be repeated herein for the sake of brevity. In some embodiments, the adjustment could be made to the operation of the sensor 60, such as adjusting the gain of the sensor, which would result in the sensor 60 sending a differing signal 1003 to the controller after the adjustment, while in other embodiments, the calibration may occur within the controller 1000, such that the controller changes the way that the signal 1003 received from the sensor 60 is processed to result in the value of the measured parameter as calculated by the controller 1000. In some embodiments where the calibration changes are made directly to the sensor's 60 operation, the changes (or instructions for the sensor 60 to change) are sent to the sensor 60 automatically via the signal path 1003.

Alternatively, the controller 1000 may generate and provide the user with instructions to manually adjust the sensor 60 to properly calibrate the sensor. The instructions may be via a display 999 upon the fryer, or a message that is relayed to the user via wireless communication, WiFi, Bluetooth, and via different types of information exchange methods (email, text, etc.).

In some embodiments, the controller 1000 may store calibration events, and in some embodiments index calibration events, such as with a date/time stamp, for future reference. In some embodiments, when a measurement of an electrical parameter of the oil by the sensor 60 is outside of a specification, or the controller detects a moving trend in the measured parameter by the sensor 60, the controller may reference the calibration history of the sensor 60, and suggest to the user that a calibration may be called for (using the portable sensor 6000), before or in conjunction with the controller 1000 taking action with respect to the oil, such as automatically initiating a filter event, dumping oil through the drain 4000, or feeding and bleeding oil, or the like.

In other embodiments, the portable sensor 6000 may communicate with the sensor 60 directly (such as via a signal path 6005 shown schematically in FIG. 3 to the antenna 70 or directly to the sensor 60), in addition to or instead of the communication with the controller 1000. In these embodiments, the sensor 60 may be programmed to self-calibrate based upon the signal received from the portable sensor 6000, rather than be calibrated based upon instructions received from the controller 1000. Other than this difference, the calibration of the sensor 60 based upon signals received from the portable sensor 6000 is consistent with the embodiments described above.

In some embodiments, as shown in FIG. 3, the cooking appliance 1 may include one or more oil quality sensors 7000 that are positioned to monitor a desired parameter of oil within the fryer pot 3 (or within one fryer pot 3 of a fryer set up where multiple neighboring fryer pots 3 are fluidly connected to one filter system and oil sensor(s) 60 disposed with respect to the filter system). The one or more oil quality sensors 7000 may be configured to measure the same parameter of oil as the sensor 60 that is positioned filter system 10, while in other embodiments, one or more sensors 7000 may be configured to measure a different parameter of oil as the sensor 60. The one or more sensors 7000 may communicate with the controller 1000 via a path 7001, which may be hard wired or wireless. In other embodiments, other than the difference between the sensor 7000 which may be rigidly mounted upon the fryer pot 3 to directly (or indirectly) measure one or more electrical characteristics of the oil within the fryer pot, the operation of the sensor 7000 and the method for calibration of the sensor 60 based upon a measurement by the sensor 7000 is consistent with the description of the operation and calibration based upon the portable sensor 6000 described above. In some embodiments, the sensor 7000 provides the measurement(s) of the electrical parameters of oil quality to the controller, with any automated operations of the fryer from the controller 1000, or indications to the user regarding oil quality based upon the measurements taken from sensor 7000. In some embodiments, the portable sensor 6000 (discussed elsewhere herein) may be used for calibrating the sensor 7000, in the same manner as discussed herein with respect to the calibration of sensor 60.

While the preferred embodiments of the disclosed have been described, it should be understood that the invention is not so limited and modifications may be made without departing from the disclosure. The scope of the disclosure is defined by the appended claims, and all devices that come within the meaning of the claims, either literally or by equivalence, are intended to be embraced therein.

The invention claimed is:

1. A system for measuring the state of degradation of cooking oil comprising:
    a vat with a receiving space configured for receipt of cooking oil, the vat movable with respect to a housing of a cooking appliance used to cook food product with cooking oil;
    a pump in fluid communication with the vat, the pump taking suction from the receiving space;
    a sensor disposed in fluid communication within the vat and adapted to measure an electrical property that is indicative of the quality of the cooking oil within the vat,
    further comprising a second sensor, the second sensor being configured to interact with oil disposed within the cooking appliance, wherein the second sensor is adapted to measure the electrical property of the cooking oil that is indicative of the quality of the cooking oil, that is measured by the sensor, wherein the second sensor is configured to send a signal to a controller that is representative of the measurement of the electrical property of the cooking oil by the second sensor, and the controller is configured to compare the measurement of the second sensor with a measurement of the electrical property of the cooking oil received from the sensor, and the controller is configured to modify a calibration of the sensor based upon a determined difference between the measurement by the sensor and the measurement by the second sensor.

2. The system of claim 1, wherein the vat comprises a plurality of wheels.

3. The system of claim 1, wherein the sensor is disposed between a filtering media disposed within the vat and the pump.

4. The system of claim 1, wherein the sensor is disposed downstream of a discharge side of the pump.

5. The system of claim 1, further comprising a valve disposed between the vat and the pump.

6. The system of claim 5, wherein the valve is a three way valve.

7. The system of claim 6, wherein the sensor is disposed within a drain line connected to a first outlet of the three way valve, wherein the receiving space is fluidly connected to a second outlet of the three way valve, and the pump is connected to a third outlet of the three way valve.

8. The system of claim 6, wherein a drain line is connected to a first outlet of the three way valve, wherein the receiving space is fluidly connected to a second outlet of the three way valve, and the sensor is fluidly connected to a third outlet of the three way valve.

9. The system of claim 8, wherein the sensor is disposed between the third outlet of the three way valve and the pump.

10. The system of claim 8, wherein the pump is disposed between the sensor and the third outlet of the three way valve.

11. The system of claim 1, wherein the pump can operate to draw suction from the receiving space of the vat in a first mode of operation and in a second mode of operation the pump can operate to discharge toward the receiving space of the vat.

12. The system of claim 1, wherein the sensor is configured to measure an electrical property that is indicative of the total polar materials of the cooking oil.

13. The system of claim 1, wherein the sensor is configured to measure the electrical property of the cooking oil when the cooking oil flows past the sensor.

14. The system of claim 1, wherein the sensor is configured to measure the electrical property of the cooking oil when the cooking oil is still with respect to the sensor.

15. The system of claim 1, wherein said sensor is selected from a capacitance sensor, a voltage sensor, a resistance sensor, a dielectric sensor, a conductivity sensor, or a conductance sensor.

16. The system of claim 1, wherein said sensor is a coaxial sensor.

17. The system of claim 1, wherein the sensor is configured to measure two or more of capacitance, voltage, resistance, dielectric, conductivity, or conductance of oil that contacts the sensor.

18. The system of claim 1, wherein the sensor is configured to communicate with a display, with the sensor providing a signal that is proportional to a measured oil quality of oil proximate to the sensor.

19. The system of claim 1, wherein the controller is configured to send a signal to the sensor to modify a setting of the sensor to modify the calibration of the sensor.

20. The system of claim 1, wherein the controller is configured to adjust its settings for processing a signal received from the sensor that is indicative of the quality of the cooking oil within the loop of piping to modify the calibration of the sensor.

21. The system of claim 1, wherein the second sensor sends the signal to the controller wirelessly.

22. The system of claim 1, the vat comprises a filtering media.

* * * * *